United States Patent
Brieden et al.

[11] Patent Number: 5,877,319
[45] Date of Patent: Mar. 2, 1999

[54] PROCESS FOR PREPARING 3-ALKOXY-5-ALKYLPYRAZIN-2-AMINES

[75] Inventors: Walter Brieden, Glis; Rudolf Fuchs, Sion, both of Switzerland

[73] Assignee: Lonza, AG, Gampel/Valais, Switzerland

[21] Appl. No.: 889,435

[22] Filed: Jul. 8, 1997

[30] Foreign Application Priority Data

Jul. 11, 1996 [CH] Switzerland ............ 1739/96
Oct. 17, 1996 [CH] Switzerland ............ 2539/96

[51] Int. Cl.$^6$ .................................. C07D 241/18
[52] U.S. Cl. .................. 544/408; 544/406; 544/409; 544/336
[58] Field of Search ............................. 544/408

[56] References Cited

U.S. PATENT DOCUMENTS

| | | | |
|---|---|---|---|
| 4,017,533 | 4/1977 | Ohtsuka | 544/408 |
| 4,193,995 | 3/1980 | Wasson et al. | 544/408 |
| 4,560,756 | 12/1985 | Brunnmueller et al. | 544/408 |
| 4,766,214 | 8/1988 | Cozzi | 544/408 |

FOREIGN PATENT DOCUMENTS 922725 4/1963 United Kingdom .

OTHER PUBLICATIONS

Taylor, E.C., et al., J. Org. Chem., vol. 46, No. 7, (1981), pp. 1394–1402.
Neilsen, et al., J. Heterocycl. Chem., vol. 24, No. 6, (1987), pp. 1621–1628.
Sato, N., et al., J. Heterocycl. Chem., vol. 25, No. 6, (1988), pp. 1737–1740.
Lumma, W.C., et al., J. Med. Chem., vol. 26, No. 3, (1989), pp. 357–363.
Sato, N., J. Heterocycl. Chem., vol. 19, No. 3, (1982), pp 673–674.
Dennin, F., et al., J. Heterocycl. Chem., vol. 27, No. 6, (1990), pp. 1639–1643.
Abignente, E., et al., Farmaco Ed. Sci., vol. 36, No. 1, (1981), pp. 61–80.
Usami, K., et al., Tetrahedron, vol. 52, No. 37, (1996), pp. 12061–12090.
Qi, C.F., et al., J. Chem. Soc. Perking Trans. 1, No. 13, (1992), pp. 1607–1612.
Sato, N., J. Heterocycl. Chem., vol. 15, No. 4, (1978), pp. 665–670.
Taylor, E.C., et al., J. Amer. Chem. Soc., vol. 95, No. 19, (1973), pp. 6413–6418.
Chemical Abstracts, vol. 16, No. 24, (1922), pp. 101–102.
E.C. Taylor et al. J. Org. Chem., (1980), pp. 2485–2489.
Taylor et al. J. Am. Chem. Soc., 95, (1973), 6413–6418.
Sato J. Heterocycl. Chem. (1985), 1145–1146.

*Primary Examiner*—Donald G. Daus
*Attorney, Agent, or Firm*—Fisher, Christen & Sabol

[57] ABSTRACT

A process for preparing 3-alkoxy-5-alkylpyrazin-2-amines of the general formula:

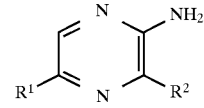

wherein $R^1$ is a $C_{1-4}$-alkyl group or an aryl group and $R^2$ is a $C_{1-4}$-alkoxy group or an aryloxy group, starting either from aminomalononitrile or from aminoacetonitrile.

18 Claims, No Drawings

PROCESS FOR PREPARING 3-ALKOXY-5-ALKYLPYRAZIN-2-AMINES

BACKGROUND OF THE INVENTION

1. Field of the Invention

The invention relates to a novel process for preparing 3-alkoxy-5-alkylpyrazin-2-amines starting either from aminomalononitrile or aminoacetonitrile and glyoxal oxime derivatives.

2. Background Art

3-Alkoxy-5-alkylpyrazin-2-amines are important intermediates for preparing pterine-6-carboxyaldehyde [E. C. Taylor and D. G. Dumas, *J. Org. Chem.*, (1980), p. 2485].

British Patent No. 922,725 describes a process for preparing 3-methoxy-5-methylpyrazin-2-amine starting from 2-amino-3-chloro-5-methylpyrazine by reaction with sodium methoxide at 130° C. A disadvantage of this process is the relatively long reaction time.

BROAD DESCRIPTION OF THE INVENTION

An object of the present invention is to provide an economical process for preparing 3-alkoxy-5-alkylpyrazin-2-amines in good yield. Other objects and advantages of the invention are set out herein or are obvious herefrom to one skilled in the art.

The objects and advantages of the invention are achieved by the process and compounds of the invention.

According to the invention, the first step of the invention process is carried out by converting aminomalononitrile, or its salt, of the formula:

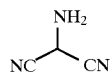
II with a glyoxal oxime derivative of the general formula:

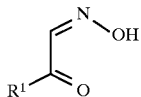
III in a manner known per se according to the method of Taylor et al. [*J. Am. Chem. Soc.*, 95, (10), (1973), 6413–6418] into an oxypyrazinecarbonitrile of the general formula:

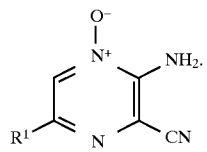
IV

The two reactants, the aminomalononitrile and the glyoxal oxime derivatives, are commercially available compounds. Aminomalononitrile tosylate is an example of an aminomalononitrile salt which can be used.

The radical $R^1$ represents $C_{1-4}$-alkyl or aryl. Suitable $C_{1-4}$-alkyls include, for example, methyl, ethyl, propyl, butyl, isobutyl or tert-butyl. Suitable aryls include phenyl and benzyl with or without substitution.

The reaction of the first step is advantageously carried out in a polar solvent. Suitable polar solvents include water, lower carboxylic acids, lower alcohols, nitriles such as acetonitrile, dimethylformamide, dimethylacetamide and dimethyl sulfoxide. Suitable lower alcohols include methanol, ethanol, propanol, isopropanol, butanol, isobutanol and tert-butanol. Suitable lower carboxylic acids include formic acid, acetic acid, propionic acid and butyric acid.

The reaction of first step is advantageously carried out under an inert gas atmosphere and at a temperature of from 0° to 180° C., preferably from 10° to 30° C.

In the second step, the oxypyrazinecarbonitrile derivative (formula IV) is hydrolyzed to give an oxypyrazinecarboxylic acid of the general formula:

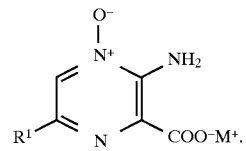
V

In the oxypyrazinecarboxylic acid salt, M represents a metal atom, for example, an alkali metal atom or an alkaline earth metal atom, or ammonium. In particular, M represents an alkali metal atom.

The hydrolysis is advantageously carried out in aqueous media and in the presence of a base or an acid. Suitable bases include alkali metal hydroxides, alkaline earth metal hydroxides or ammonium salts. Suitable alkali metal hydroxides include sodium hydroxide and potassium hydroxide. Suitable alkaline earth metal hydroxides include calcium hydroxide and magnesium hydroxide. Suitable acids include sulfuric acid and hydrohalic acids such as HCl, HBr and HI. The hydrolysis is preferably carried out in the presence of a base.

The hydrolysis is advantageously carried out under an inert gas atmosphere and at a temperature from 0° to 100° C. The hydrolysis is preferably carried out at a temperature from 50° to 80° C.

In the third step, the oxypyrazinecarboxylic acid salt (formula V) is halogenated to give a halooxypyrazine of the general formula:

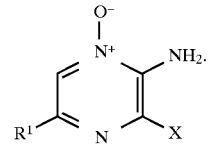
VI

The substituent X represents a halogen atoms such as fluorine, chlorine, bromine or iodine. The halogenation may be carried out using a halogen or halooxy acids or salts thereof. Suitable halogens include $Cl_2$, $Br_2$ and $I_2$; preference is given to $Br_2$. Suitable halooxy acids include the following: HClO, HBrO, HIO, $HClO_3$, $HBrO_3$ and $HIO_3$, and alkali metal salts thereof such as KOBr and $NaBrO_3$.

The halogenation of step three is advantageously carried out at a temperature of from −30° to 100° C., preferably at a temperature of from 0° to 30° C.

Suitable solvents for the halogenation are polar solvents such as water, lower alcohols or aqueous lower alcohols. Suitable lower alcohols include methanol, ethanol, propanol and butanol.

In the fourth step, the halooxypyrazinamine (formula VI) is converted into a 3-alkoxy-5-alkyl-1-oxypyrazin-2-ylamine of the general formula:

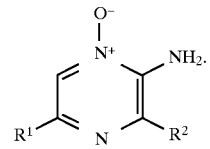
VII wherein $R^1$ is as defined above, and $R^2$ is a $C_{1-4}$-alkoxy group or an aryloxy group, using either an alcohol in the presence of a base.

Suitable C$_{1-4}$-alkoxy groups include methoxy, ethoxy, propoxy, isopropoxy, butoxy, isobutoxy and tert-butoxy. Suitable aryloxy groups include phenyloxy and benzyloxy with or without substitution.

Suitable bases include alkali metal hydroxides, alkaline earth metal hydroxides, ammonium salts or alkoxides. Suitable alkali metal hydroxides include sodium hydroxide and potassium hydroxide. Suitable alkaline earth metal hydroxides include calcium hydroxide and magnesium hydroxide.

The corresponding alkali metal C$_{1-4}$-alkoxides or alkali metal aryl alkoxides are advantageously employed as alkoxides. Suitable alkali metal C$_{1-4}$-alkoxides include sodium methoxide, potassium methoxide, sodium ethoxide, potassium ethoxide, sodium propoxide, potassium propoxide, sodium butoxide and potassium butoxide. Suitable alkali metal aryl alkoxides include sodium phenoxide, potassium phenoxide, sodium benzyl alkoxide and potassium benzyl alkoxide. The corresponding C$_{1-4}$-alcohols or aryl alcohols, for example, methanol, ethanol, propanol, isopropanol, butanol, tert-butanol, isobutanol, phenol or benzyl alcohol, are advantageously employed as the alcohol. Suitable bases include the same bases as mentioned for step two.

In step four, the corresponding alcohol or the corresponding aqueous alcohol is usually employed as solvent.

The reaction of step four is advantageously carried out under an inert gas atmosphere and at a temperature of from 0° to 180° C., preferably at a temperature of from 20° to 80° C.

In step 5, the 3-alkoxy-5-alkyl-1-oxypyrazin-2-ylamine (formula VII) is reduced to give the end product of general formula I.

The reduction of step five is advantageously carried out catalytically using hydrogen, PCl$_3$ or Na$_2$S$_2$O$_4$, preferably catalytically using hydrogen.

Suitable hydrogenation catalysts include noble metal, noble metal oxide and Raney catalysts, which if appropriate are deposited on a carrier. Examples of hydrogenation catalysts include Raney nickel, platinum on carbon or platinum on aluminum oxide. It is advantageous to employ platinum on carbon, in particular 1 to 10 percent by weight of platinum on carbon, as the hydrogenation catalyst. The hydrogenation catalysts can be employed in amounts of from 0.1 to 40 percent by weight, preferably from 5 to 20 percent by weight, based on the 3-alkoxy-5-alkyl-1-oxypyrazin-2-ylamine. The hydrogenation is advantageously carried out at an elevated H$_2$ pressure, preferably at a pressure from 1 to 10 bar.

The reduction of step 5 is advantageously carried out in a polar solvent. Suitable polar solvents include, for example, lower alcohols, water, dimethylformamide and carboxylic acids. Suitable lower alcohols are the same as mentioned for step three. Suitable carboxylic acids include, for example, formic acid and acetic acid.

The reaction is advantageously carried out under an inert gas atmosphere and at a temperature of from 0° to 250° C., preferably of from 120° to 180° C.

In a preferred embodiment, the entire process is carried out without isolation of the oxypyrazine-carboxylate salt (formula V).

In a further embodiment according to the invention, the first process step is carried out in such a way that aminoacetonitrile or a salt thereof of the formula:

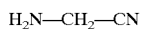  VIII is converted with a glyoxal oxime derivative of the general formula:

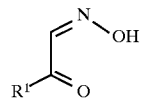

wherein R$^1$ is as defined above, in the presence of a base in a manner known per se by the method of J. Heterocycl. Chem., (1985), 1145–1146, into an oxypyrazinamine of the general formula:

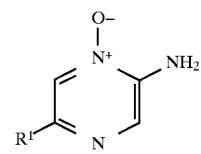

wherein R$^1$ is as defined above.

The reactant aminoacetonitrile is commercially available. Suitable aminoacetonitrile salts include its hydrochloride and hydrobromide salts.

Suitable bases include methylmorpholine, triethylamine, pyridine, an alkali metal hydroxide, an alkoxide or an alkali metal carbonate. Suitable alkoxides are the same as used in step four. Suitable alkali metal hydroxides are the same as used in step two. Suitable alkali metal carbonates include sodium carbonate and potassium carbonate.

According to this process variant, the reaction of step one is advantageously carried out in a polar solvent. Suitable polar solvents include halogenated hydrocarbons, such as, dichloromethane, chloroform, carbon tetrachloride, trichloroethane, tetrachloroethane, ethylene chloride and (hydro)chlorofluorocarbons, the lower alcohols described above, the lower carboxylic acids described above, water, dimethylformamide and dimethylacetamide.

The reaction of step one is advantageously carried out under an inert gas atmosphere and at a temperature of from −30° to 100° C., preferably of from 0° to 40° C.

In the second step of this process variant, the oxypyrazinamine (formula IX) is halogenated to give a halooxypyrazinamine of the general formula:

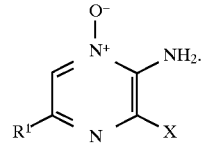

wherein R$^1$ and X are each as defined above.

Suitable halogenating reagents and suitable solvents for the halogenation include those used in the variant described above.

According to this variant, the halogenation is advantageously carried out at a temperature of from −30° to 100° C., preferably at a temperature of from 0° to 30° C.

The other reaction steps of this process variant are carried out similarly to the variant described above, i.e., the third step of this variant is carried out similarly to the fourth step of the variant described above and the fourth step of this variant is carried out similarly to the fifth step of the variant described above.

This process variant is advantageously carried out without isolation of the intermediate of the formula VI.

The oxypyrazinecarboxylic acid salts (formula V), the halooxypyrazinamines (formula VI) and the 3-alkoxy-5-alkyl-1-oxypyrazin-2-ylamine (formula VII) have not been described in the literature and, thus, as novel intermediates for preparing 3-alkoxy-5-alkylpyrazin-2-amines, form part of the subject matter of the invention.

M in the oxypyrazinecarboxylic acid salt advantageously represents an alkali metal atom such as sodium or potassium.

The substituent X in the halooxypyrazinamine (formula VI) is as defined above and advantageously represents bromine.

The radical $R^1$ in the halooxypyrazinamine (formula VI) and in the 3-alkoxy-5-alkyl-1-oxypyrazin-2-ylamine (formula VII) is as defined above and advantageously represents $C_{1-4}$-alkyl, preferably methyl. In the 3-alkoxy-5-alkyl-1-oxypyrazin-2-ylamine (formula VII), $R^2$ is as defined above and advantageously represents $C_{1-4}$-alkoxy, preferably methoxy.

Thus, the most preferred compounds are 3-bromo-5-methyl-1-oxypyrazin-2-ylamine (formula VI) and 3-methoxy-5-methyl-1-oxypyrazin-2-ylamine (formula VII).

DETAILED DESCRIPTION OF THE INVENTION

EXAMPLE 1

Preparation of 3-amino-6-methyl-4-oxypyrazine-2-carbonitrile 34.80 g of anti-methylglyoxal 1-oxime (391.6 mmol) and 98.15 g of aminomalononitrile toluene-4-sulfonate (379 mmol) were charged initially with 600 ml of isopropanol into a 1000 ml flask under argon, and stirred at 20° C. for 4 hours. After cooling to 5° C., the product was filtered and washed with 40 ml of cold water and 40 ml of cold ethanol. After drying, a crude product (55.28 g) was obtained. The crude product was stirred for 30 minutes at 85° C. in 150 ml of ethanol (slurry). The product was filtered at 14° C. and dried. 53.35 g of 3-amino-6-methyl-4-oxypyrazine-2-carbonitrile was obtained. The yield of the product was 91.3 percent. Other data concerning the product was:

$^1$H NMR (DMSO-$d_6$, 400 MHz)δ: 2.29 (s, 3H); 7.70 (s, 2H); 8.45 (s, 1H). Melting point: 187°–188° C.

EXAMPLE 2

Preparation of 3-amino-6-phenyl-4-oxypyrazine-2-carbonitrile 25.1 g of isonitrosoacetophenone (167.4 mmol) and 41.9 g of aminomalononitrile toluene-4-solfonate (162.1 mmol) were charged initially with 250 ml of isopropanol into a 500 ml flask under argon, and stirred at 20° C. for 4 hours. After cooling to 5° C., the product was filtered and washed with 40 ml of cold water and 40 ml of cold ethanol. After drying, a crude product (33.12 g) was obtained. The crude product was three times slurried up in 100 ml of water at 20° C. and then filtered. 11 g of 3-amino-6-phenyl-4-oxypyrazine-2-carbonitrile was obtained. The yield of the product was 32 percent. Other data concerning the product was:

$^1$H NMR (DMSO-$d_6$, 400 MHz)δ: 7.45 (m, 3H); 7.97 (m, 2H); 8.05 (s, 2H); 9.18 (s, 1H). $^{13}$C NMR (DMSO-$d_6$, 400 MHz)δ: 149.519; 142.298; 134.147; 131.306; 129.286; 128.797; 125.609; 115.106; 11.184

EXAMPLE 3

Preparation of 3-bromo-5-methyl-1-oxopyrazin-2-ylamine without isolation of intermediate (formula V)

3-Amino-6-methyl-4-oxopyrazine-2-carbonitrile (10.04 g; 66.8 mmol), KOH (5.23 g, 85 percent pure) (86.3 mmol) and water (66 g) were charged initially in a 250 ml flask under argon and heated to 45° C. for 3 hours. 10.6 g of bromine (66.3 mmol) was then added dropwise over 30 minutes at 18° C. (exothermic reaction and gas formation). The temperature increased to 28° C. The mixture was stirred at 20° C. for 1 hour, and 40 ml of n-butanol was added for the extraction. After the phase separation, the mixture was twice extracted with 30 ml of n-butanol each time. The organic phase was concentrated completely. After drying, 9.4 g of 3-bromo-5-methyl-1-oxopyrazin-2-ylamine was obtained. The yield of the product was 68 percent. Other data concerning the product was:

$^1$H NMR (DMSO-$d_6$, 400 MHz)δ: 2.15 (s, 3H); 6.90 (s, 2H); 8.18 (s, 1H).

EXAMPLE 4

Preparation of 3-methoxy-5-methyl-1-oxypyrazin-2-ylamine (a) Under argon, the 3-bromo-5-methyl-1-oxopyrazin-2-ylamine (3.57 g; 16.8 mmol) and methanol (50 ml) were charged initially. At 20° C., a solution of sodium methoxide (3.47 g; 19.2 mmol) was added dropwise over 15 minutes. The mixture was stirred at 62° C. for 2 hours. The solvent was completely removed by distillation. According to NMR analysis, 3-methoxy-5-methyl-1-oxypyrazin-2-ylamine was obtained. The yield of the product was 90 percent.

(b) Under argon, 3-bromo-5-methyl-1-oxopyrazin-2-ylamine (4.2 g; 20 mmol), methanol (22.5 g), water (21.2 g) and KOH (1.4 g; 21.2 mmol) were charged initially in a flask. At 70° C., the mixture was stirred for 3.5 hours. The methanol was distilled off and the product was three times extracted with 20 ml of n-butanol each time. 3.07 g of 3-methoxy-5-methyl-1-oxypyrazin-2-ylamine was obtained. The yield of the product was 99 percent. Other data concerning the product was:

$^1$H NMR (DMSO-$d_6$, 400 MHz)δ: 2.10 (s, 3H); 3.96 (s, 3H); 6.50 (s, 2H); 7.66 (s, 1 H).

EXAMPLE 5

Preparation of 3-methoxy-5-methylpyrazin-2-amine

3-Methoxy-5-methyl-1-oxopyrazin-2-ylamine (1 g; 6.44 mmol) and methanol (50 ml) were charged initially together with 0.19 g of Pt/C-5 percent into an autoclave. The autoclave was first flushed with argon (three times), and a hydrogen pressure of 10 bar was then applied. The hydrogenation proceeded for 5 hours at 130° C. At 20° C., the autoclave was flushed with argon. The catalyst was filtered and washed with 5 ml of methanol. The solvent was completely removed by distillation. 0.85 g of 3-methoxy-5-methylpyrazin-2-amine was obtained. The yield of the product was 95 percent. Other data concerning the product was:

$^1$H NMR (DMSO-$d_6$, 400 MHz)δ: 2.20 (s, 3H); 3.87 (s, 3H); 5.90 (s, 2H); 7.33 (s, 1H). Melting point: 75°–76.5° C.

EXAMPLE 6

Preparation of 5-methyl-1-oxypyrazin-2-amine

Isonitrosoacetone (18.7 g; 0.21 mol) and methylmorpholine (22.0 g; 0.213 mol) were charged initially with chloroform (200 ml) into a flask under argon. At 65° C., aminoacetonitrile hydrochloride (24.35 g; 0.257 mol) was added a little at a time over 2 hours, and stirring was continued for a further 2 hours at this temperature. At 20° C., water (80 ml) and HCl (32 percent strength; 12.9 g) were then added. The crude solution was filtered through celite and the phases were then separated. The aqueous phase was adjusted to pH 11 using NaOH (30 percent strength; 71.0 g). The product was extracted with 2-methyl-2-butanol (4 times 60 ml each time) at 40° C. The organic phase was completely removed by distillation. 7.68 g of the product, corresponding to a yield of 30 percent, was obtain. Other data concerning the product was:

NMR (DMSO-$d_6$) (400 MHz): 2.24 (s, 3H); 6.70 (s, 2H); 8.02 (s, 2H).

EXAMPLE 7

Preparation of 3-methoxy-5-methyl-1-oxypyrazin-2-ylamine (without isolation of 3-bromo-5-methyl-1-oxypyrazin-2-ylamine)

(a) 5-methyl-1-oxypyrazin-2-amine (2.0 g; 15.9 mmol), KOH (85 percent pure; 1.21 g; 18.3 mmol), water (6 g) and methanol (9.5 g) were initially charged in a flask under argon. At 3° C., bromine (4.92 g; 30.7 mmol) was then added dropwise over 30 minutes. The temperature increased to 10° C. The mixture was stirred at 20° C. for 1 hour, and KOH (64 mmol) and methanol (7.9 g) were added. The mixture was then stirred at 72° C. for 2 hours. The methanol was distilled off and the product was extracted with 2-methyl-2-butanol (3 times 40 ml each time). The organic phase was concentrated completely. After drying, 1.58 g of the product, corresponding to a yield of 63 percent, was obtained. Other data concerning the product was:

NMR (DMSO-$d_6$) (400 MHz): 2.10 (s, 3H); 3.96 (s, 3H); 6.50 (s, 2H); 7.66 (s, 1H).

(b) The 3-amino-6-methyl-4-oxopyrazine-2-carbonitrile (20 g; 129.8 mmol), KOH (13.36 g; 85 percent pure) (203.9 mmol) and water (130 g) were charged initially in a flask under argon and heated to 45° C. for 3 hours. At 9° C., 33.58 g of bromine (210 mmol) and 25 g of methanol were then added dropwise over 30 minutes (exothermic reaction and formation of gas). The temperature increased to 13° C. The mixture was stirred at 20° C. for 1 hour, and 19.14 g of KOH (290 mmol) and 63 g of methanol were added. The mixture was stirred at 72° C. for 2 hours. The methanol was distilled off and the product was extracted continuously with 2-methyl-2-butanol. The 3-methoxy-5-methyl-1-oxopyrazin-2-ylamine precipitated in 2-methyl-2-butanol. After filtration at 5° C. and drying, 21.05 g of 3-methoxy-5-methyl-1-oxopyrazin-2-ylamine was obtained. The yield of the product was 82 percent.

What is claimed is:

1. A process for preparing a 3-alkoxy-5-alkylpyrazin-2-amine of formula:

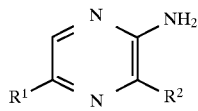

I wherein $R^1$ represents a $C_{1-4}$-alkyl group or phenyl or benzyl or substituted phenyl or substituted benzyl, and $R^2$ represents a $C_{1-4}$-alkoxy or phenyloxy or benzyloxy or substituted phenyloxy or substituted benzyloxy, comprising the steps of, in a first step, converting aminomalononitrile, or a salt thereof, of formula:

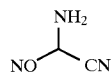

II with a glyoxal oxime compound of formula:

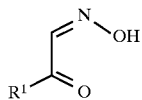

III wherein $R^1$ is as defined above, in a manner known per se into an oxypyrazinecarbonitrile compound of formula:

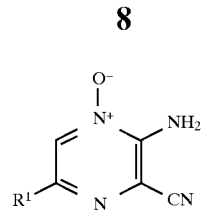

IV wherein $R^1$ is as defined above, in a second step, hydrolyzing the oxypyrazinecarbonitrile derivative of formula IV in the presence of an acid or a base (a) to give an oxypyrazinecarboxylic acid salt of formula:

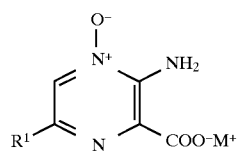

V wherein $R^1$ is as defined above, and M is a metal atom or ammonium, in a third step, halogenating the oxypyrazinecarboxylic acid step of formula V to give a halooxypyrazinamine of formula:

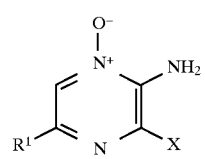

VI wherein $R^1$ is as defined above, and X is a halogen atom, in a fourth step, converting the halooxypyrazinamine of formula VI with an alcohol in the presence of a base (b) into a 3-alkoxy-5-alkyl-1-oxypyrazin-2-ylamine of formula:

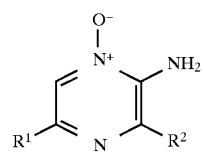

VII wherein $R^1$ and $R^2$ are each as defined above, and, in a fifth step, reducing the 3-alkoxy-5-alkyl-1-oxypyrazin-2-ylamine of formula VII to give the end product of formula I.

2. The process according to claim 1, wherein the hydrolysis of step two is carried out in the presence of an acid.

3. The process according to claim 1, wherein the base (a) used in the second step is an alkali metal hydroxide, an alkaline earth metal hydroxide or an ammonium salt.

4. The process according to claim 3, wherein the base (b) used in the fourth step is an alkali metal hydroxide, an alkaline earth metal hydroxide or an ammonium salt.

5. The process according to claim 4, wherein the base (b) used in the fourth step is an alkoxide.

6. The process according to claim 5, wherein the alkoxide used in the fourth step is an alkali metal $C_{1-4}$-alkoxide or an alkali metal aryl alkoxide.

7. The process according to claim 4, wherein the base (a) in the second step and the base (b) in the fourth step are the same.

8. The process according to claim 5, wherein the reduction of the fifth step is carried out catalytically with hydrogen, $PCl_3$ or $Na_2S_2O_4$.

9. The process according to claim 8, wherein the hydrogenation catalyst used in the fifth step is platinum on carbon.

10. The process according to claim 9, wherein the reaction of the second step is carried out without isolation of the intermediate of formula V.

11. The process according to claim 1, wherein the base (a) used in the second step is an alkali metal hydroxide, an alkaline earth metal hydroxide or an ammonium salt.

12. The process according to claim 1, wherein the base (b) used in the fourth step is an alkali metal hydroxide, an alkaline earth metal hydroxide or an ammonium salt.

13. The process according to claim 1, wherein the base (b) used in the fourth step is an alkoxide.

14. The process according to claim 13, wherein the alkoxide used in the fourth step is an alkali metal $C_{1-4}$-alkoxide or an alkali metal aryl alkoxide.

15. The process according to claim 1, wherein the base (a) used in the second step and the base (b) used in the fourth step are the same.

16. The process according to claim 1, wherein the reduction of the fifth step is carried out catalytically with hydrogen, $PCl_3$ or $Na_2S_2O_4$.

17. The process according to claim 1, wherein the hydrogenation catalyst used in the fifth step is platinum on carbon.

18. The process according to claim 1, wherein the reaction is carried out without isolation of the intermediate of formula V.

* * * * *